United States Patent
Hasegawa et al.

(10) Patent No.: US 10,119,489 B2
(45) Date of Patent: Nov. 6, 2018

(54) DIAGNOSTIC DEVICE AND DIAGNOSTIC SYSTEM

(71) Applicant: ISUZU MOTORS LIMITED, Tokyo (JP)

(72) Inventors: Ken Hasegawa, Saitama (JP); Hirotaka Takahashi, Hiratsuka (JP); Masanobu Minezawa, Yokohama (JP)

(73) Assignee: ISUZU MOTORS LIMITED, Tokyo (JP)

( * ) Notice: Subject to any disclaimer, the term of this patent is extended or adjusted under 35 U.S.C. 154(b) by 0 days.

(21) Appl. No.: 15/553,940

(22) PCT Filed: Feb. 24, 2016

(86) PCT No.: PCT/JP2016/055457
§ 371 (c)(1),
(2) Date: Aug. 25, 2017

(87) PCT Pub. No.: WO2016/136818
PCT Pub. Date: Sep. 1, 2016

(65) Prior Publication Data
US 2018/0038304 A1 Feb. 8, 2018

(30) Foreign Application Priority Data
Feb. 27, 2015 (JP) .................. 2015-038864

(51) Int. Cl.
*F02D 41/00* (2006.01)
*F02D 41/22* (2006.01)
(Continued)

(52) U.S. Cl.
CPC ......... *F02D 41/222* (2013.01); *F01N 13/008* (2013.01); *F02D 41/2441* (2013.01);
(Continued)

(58) Field of Classification Search
CPC .... F02D 41/222; F02D 41/3005; F02D 13/04; F02D 41/2448; F01N 13/008; F01N 2560/026; G01N 33/0037
See application file for complete search history.

(56) References Cited

U.S. PATENT DOCUMENTS

2009/0229356 A1  9/2009 Kariya et al.
2011/0138874 A1  6/2011 Murase
(Continued)

FOREIGN PATENT DOCUMENTS

JP  2002-539448 T  11/2002
JP  2009-216042 A   9/2009
(Continued)

OTHER PUBLICATIONS

International Search Report and Written Opinion for PCT App No. PCT/JP2016/055457 dated May 10, 2016, 9 pgs.

*Primary Examiner* — Thomas Moulis
(74) *Attorney, Agent, or Firm* — Procopio, Cory, Hargreaves & Savitch LLP

(57) ABSTRACT

A diagnostic device for a sensor 100 provided in an exhaust passage 11 of an internal combustion engine 10 of a vehicle and detecting nitrogen compounds in exhaust gas, the diagnostic device including an offset diagnosis unit 42 which diagnoses, during deceleration of the vehicle in which the internal combustion engine 10 stops fuel injection, an offset amount of a sensor value of the sensor 100 from a zero point based on the sensor value of the sensor value, and a diagnosis prohibition unit 44 which prohibits the diagnosing of the offset amount when a flow rate of the exhaust gas of the internal combustion engine 10 rapidly increases while the offset amount is diagnosed by the offset diagnosis unit 42.

6 Claims, 4 Drawing Sheets

(51) Int. Cl.
*F02D 41/30* (2006.01)
*G01N 33/00* (2006.01)
*F01N 13/00* (2010.01)
*F02D 41/24* (2006.01)
*F02D 13/04* (2006.01)

(52) U.S. Cl.
CPC ..... *F02D 41/3005* (2013.01); *G01N 33/0037* (2013.01); *F01N 2560/026* (2013.01); *F02D 13/04* (2013.01)

(56) References Cited

U.S. PATENT DOCUMENTS

2011/0271663 A1* 11/2011 Sato ................. F01N 3/103
 60/295
2017/0106338 A1* 4/2017 Singh ................ B01D 53/9495

FOREIGN PATENT DOCUMENTS

| JP | 2010-071195 A | 4/2010 |
| JP | 2013-185575 A | 9/2013 |

* cited by examiner

DIAGNOSTIC DEVICE AND DIAGNOSTIC SYSTEM

CROSS-REFERENCE TO RELATED APPLICATIONS

This application is a U.S. National Stage entry of PCT Application No. PCT/JP2016/055457, filed on Feb. 24, 2016, which claims priority to Japanese Patent Application No. 2015-038864, filed Feb. 27, 2015, the contents of which are incorporated herein by reference.

TECHNICAL FIELD

The present invention relates to a diagnostic device and a diagnostic system, and in particular, to a diagnostic device and a diagnostic system for a NOx sensor that detects nitrogen compounds (hereinafter, NOx) in exhaust gas discharged from an internal combustion engine.

BACKGROUND ART

In general, as diagnostic devices of such a type, a device is known which executes offset diagnosis of diagnosing an offset amount of a sensor value from a zero point, in a state where a concentration of NOx contained in exhaust gas becomes substantially 0 (zero) due to stop of fuel injection by an engine during deceleration of a vehicle or the like (e.g., see Patent Reference 1).

PRIOR ART REFERENCE

Patent Reference

Patent Reference 1: JP-A-2009-216042

DISCLOSURE OF THE INVENTION

Problems to be Solved

However, among large vehicles such as trucks, a vehicle is known which is mounted with an exhaust brake device which obtains a braking force by closing an exhaust flow path with an exhaust brake valve and thus increasing an exhaust resistance during deceleration of the vehicle, as an auxiliary brake for a service brake. When the exhaust brake device is switched from an operation state (on) to a non-operation state (off), the exhaust brake valve is opened and thus a flow rate of the exhaust gas rapidly increases.

In such a state where the flow rate of the exhaust gas rapidly increases, there is a case where a delay in internal processing of the NOx sensor occurs and thus a sensor value instantaneously rapidly increases relative to an actual NOx value and indicates an abnormal value. In this state, if the offset diagnosis as described above is executed, there is a problem that an erroneous diagnosis in which the abnormal value is recognized as the offset amount from the zero point is caused.

An object of the present disclosure is to provide a diagnostic device and a diagnostic system, which effectively prevent an erroneous diagnosis in the offset diagnosis caused when a flow rate of the exhaust gas rapidly increases.

Means for Solving the Problems

According to the present disclosure, there is provided a diagnostic device for a sensor provided in an exhaust passage of an internal combustion engine of a vehicle and detecting nitrogen compounds in exhaust gas, the diagnostic device including: an offset diagnosis unit which diagnoses, during deceleration of the vehicle in which the internal combustion engine stops fuel injection, an offset amount of a sensor value of the sensor from a zero point based on the sensor value of the sensor; and a diagnosis prohibition unit which prohibits the diagnosing of the offset amount when a flow rate of the exhaust gas of the internal combustion engine rapidly increases while the offset amount is diagnosed by the offset diagnosis unit.

It is preferable that the diagnosis prohibition unit prohibits the diagnosing of the offset amount when an exhaust brake device is switched from an operation state to a non-operation state.

It is preferable that the diagnosis prohibition unit prohibits the diagnosing of the offset amount until a predetermined period of time has passed after switching to the non-operation state when the exhaust brake device is switched from the operation state to the non-operation state.

Also, according to the present disclosure, there is provided a diagnostic system including: a sensor provided in an exhaust passage of an internal combustion engine of a vehicle and detecting nitrogen compounds in exhaust gas; and a control unit, wherein the control unit is operated to execute: an offset diagnosis process of diagnosing, during deceleration of the vehicle in which the internal combustion engine stops fuel injection, an offset amount of a sensor value of the sensor from a zero point based on the sensor value of the sensor, and a diagnosis prohibition process of prohibiting the diagnosing of the offset amount when a flow rate of the exhaust gas of the internal combustion engine rapidly increases while the offset amount is diagnosed by the offset diagnosis process.

It is preferable that, in the diagnosis prohibition process, the control unit prohibits the diagnosing of the offset amount when an exhaust brake device is switched from an operation state to a non-operation state.

It is preferable that, in the diagnosis prohibition process, the control unit prohibits the diagnosing of the offset amount until a predetermined period of time has passed after switching to the non-operation state when the exhaust brake device is switched from the operation state to the non-operation state.

Advantageous Effects of Invention

According to the diagnostic device and the diagnostic system of the present disclosure, it is possible to effectively prevent an erroneous diagnosis in the offset diagnosis caused when a flow rate of the exhaust gas rapidly increases.

MODE FOR CARRYING OUT THE INVENTION

Figure 1:
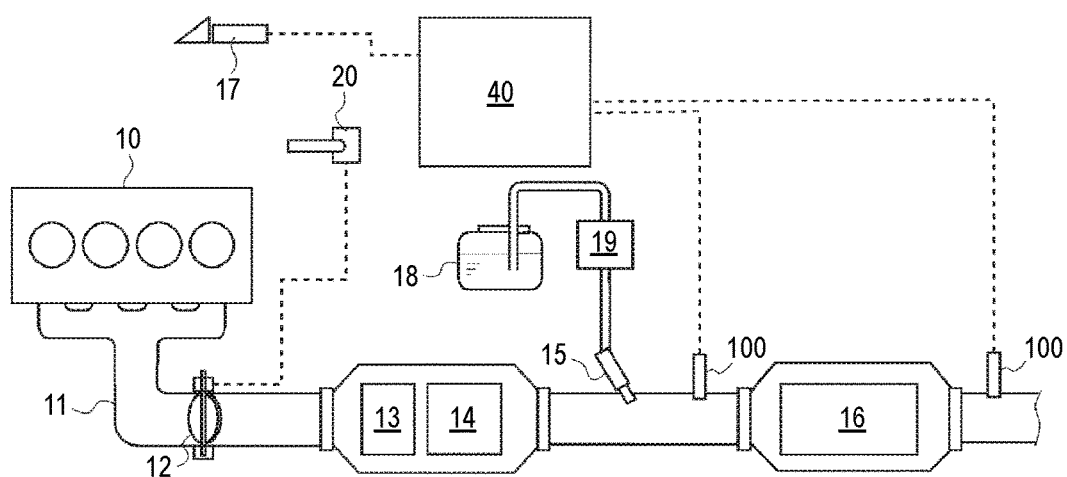
FIG. 1 is a schematic configuration view showing an example of an exhaust system of an internal combustion engine, to which a diagnostic device of the present embodiment is applied.

Hereinafter, a diagnostic device according to one embodiment of the present invention will be described with reference to the accompanying drawings. The same components will be designated by the same reference numerals, and the names and functions thereof are the same. Therefore, the detailed descriptions thereof will not be repetitively made.

FIG. 1 is a schematic configuration view showing an example of an exhaust system of an internal combustion engine (hereinafter, simply referred to as engine) 10, to which a diagnostic device according to the present embodiment is applied. In an exhaust passage 11, an exhaust brake valve 12 configuring a part of an exhaust brake device, an oxidation catalyst 13, a particulate filter 14, an urea adding valve 15, an selective catalytic reduction catalyst (hereinafter, referred to as SCR catalyst) 16 and the like are provided in this order from an upstream side in an exhaust direction. A NOx sensor 100 of the present embodiment is provided in the exhaust passage 11 downstream of the exhaust brake valve 12 and at least one of upstream and downstream of the SCR catalyst 16. Meanwhile, in FIG. 1, a reference numeral 40 refers to a control unit, a reference numeral 17 refers to an accelerator opening sensor, a reference numeral 18 refers to an urea water tank, a reference numeral 19 refers to a urea water pump and a reference numeral 20 refers to an exhaust brake switch provided in a driver's cabin (not shown).

Figure 2:
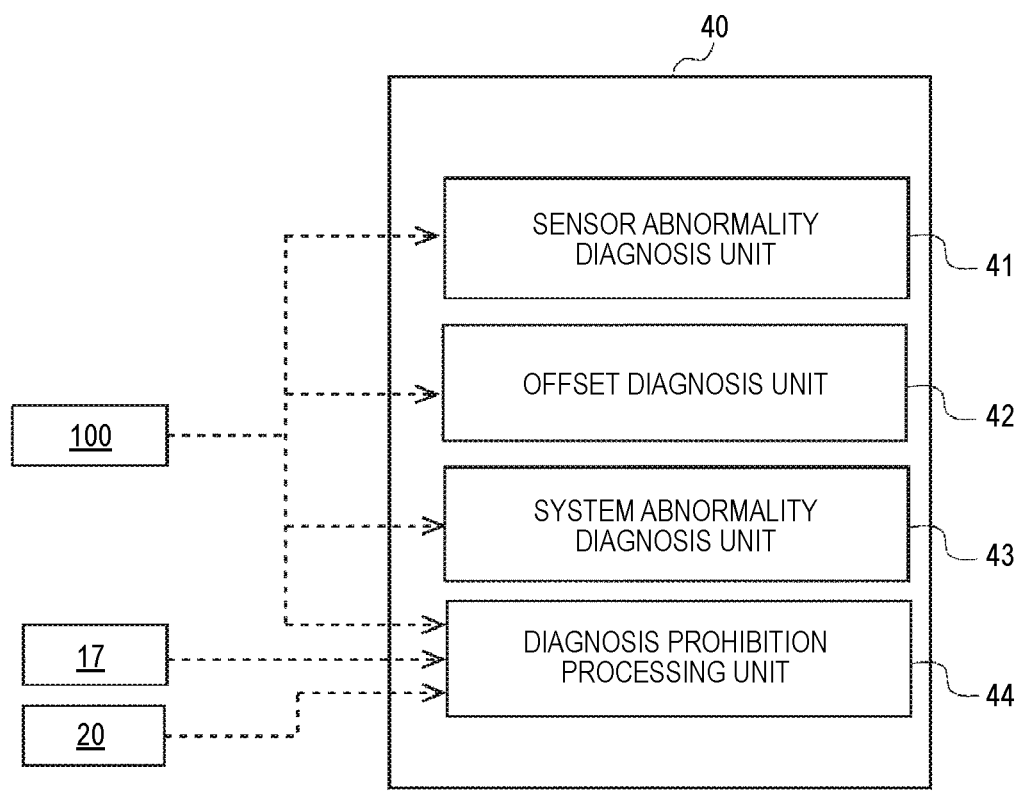
FIG. 2 is a functional block diagram showing a control unit of the present embodiment.

The control unit 40 includes a CPU, a ROM, a RAM, an input port, an output port and the like, which are well known. According to the present embodiment, the control unit 40, as shown in FIG. 2, has a sensor abnormality diagnosis unit 41, an offset diagnosis unit 42, a system abnormality diagnosis 43 and a diagnosis prohibition processing unit 44 as parts of functional elements. In the present embodiment, the functional elements are described as being contained in the control unit 40, which is a unitary hardware, but some thereof may be provided in separate hardware.

Figure 3A:
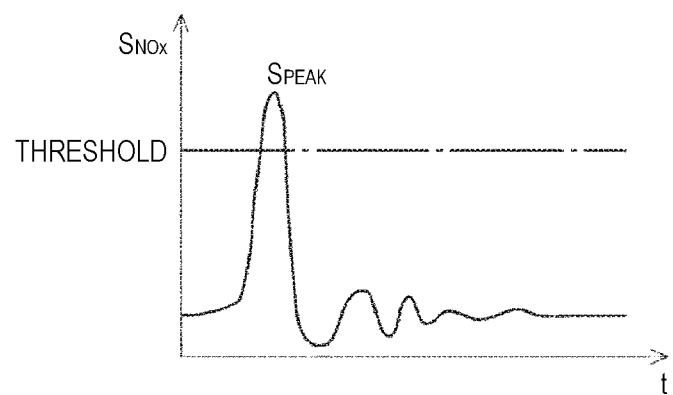
FIG. 3A is a time chart explaining a sensor failure diagnosis of the present embodiment.
Figure 3B:
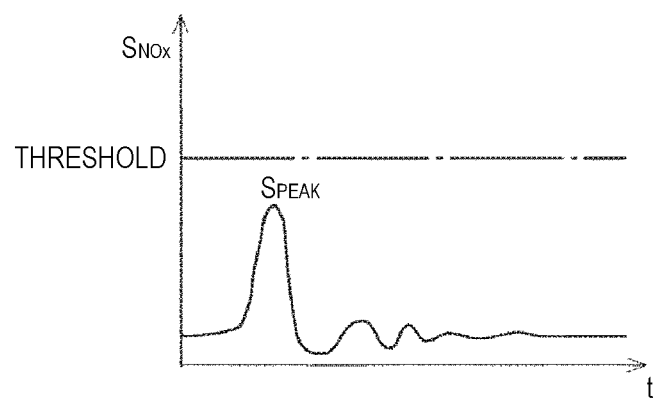
FIG. 3B is a time chart explaining a sensor failure diagnosis of the present embodiment.

The sensor abnormality diagnosis unit 41 is configured to diagnose whether or not an abnormality has occurred in the NOx sensor 100, based on a sensor value $S_{NOx}$ of the NOx sensor 100. More specifically, when an abnormal value, which is different from an actual NOx concentration, is instantaneously outputted as the sensor value $S_{NOx}$ of the NOx sensor 100, it is determined that an abnormality has occurred in the NOx sensor 100 in a case where a peak value $S_{PEAK}$ thereof has exceeded a predetermined threshold (see FIG. 3A). In contrast, if the peak value $S_{PEAK}$ is equal to or lower than the predetermined threshold (see FIG. 3B), it is determined that the NOx sensor 100 is normal.

The offset diagnosis unit 42 is configured to execute offset diagnosis of diagnosing an offset amount of the sensor value $S_{NOx}$ of the NOx sensor 100 from a zero point, in a state where, during deceleration of the vehicle or the like, the engine 10 has stopped fuel injection and thus a NOx value in the exhaust gas has become substantially zero. Whether or not the engine 10 has stopped the fuel injection may be detected based on a sensor value of the accelerator opening sensor 17.

The system abnormality diagnosis unit 43 is configured to execute system abnormality diagnosis of detecting a significant decline in NOx purification performance of the SCR catalyst 16, a failure of the urea adding value 15 and the like, based on the sensor value $S_{NOx}$ of the NOx sensor 100.

The diagnosis prohibition processing unit 44 is configured to prohibit the system abnormality diagnosis by the system abnormality diagnosis unit 43 in a case where the sensor abnormality diagnosis unit 41 determines that an abnormality has occurred in the NOx sensor 100. Also, even if the sensor abnormality diagnosis unit 41 determines that the NOx sensor 100 is normal, the diagnosis prohibiting processing unit 44 is configured to prohibit the offset diagnosis by the offset diagnosis unit 42 until a predetermined period of time has passed from a time when the exhaust brake device is switched from an operation state (on) to a non-operation state (off).

More specifically, in a case where a flow rate of the exhaust gas has rapidly increased due to switching of the exhaust brake device from on to off and thus an abnormal value is instantaneously outputted as the sensor value $S_{NOx}$ of the NOx sensor 100, if the peak value $S_{PEAK}$ thereof is equal to or lower than the threshold, the diagnosis prohibition processing unit 44 prohibits the offset diagnosis during a predetermined period of time (e.g., about 4 to 5 seconds) until the sensor value $S_{NOx}$ is stabilized. Therefore, it is possible to effectively prevent an erroneous diagnosis in the offset diagnosis caused when the exhaust brake is used during deceleration of the vehicle.

Figure 4:
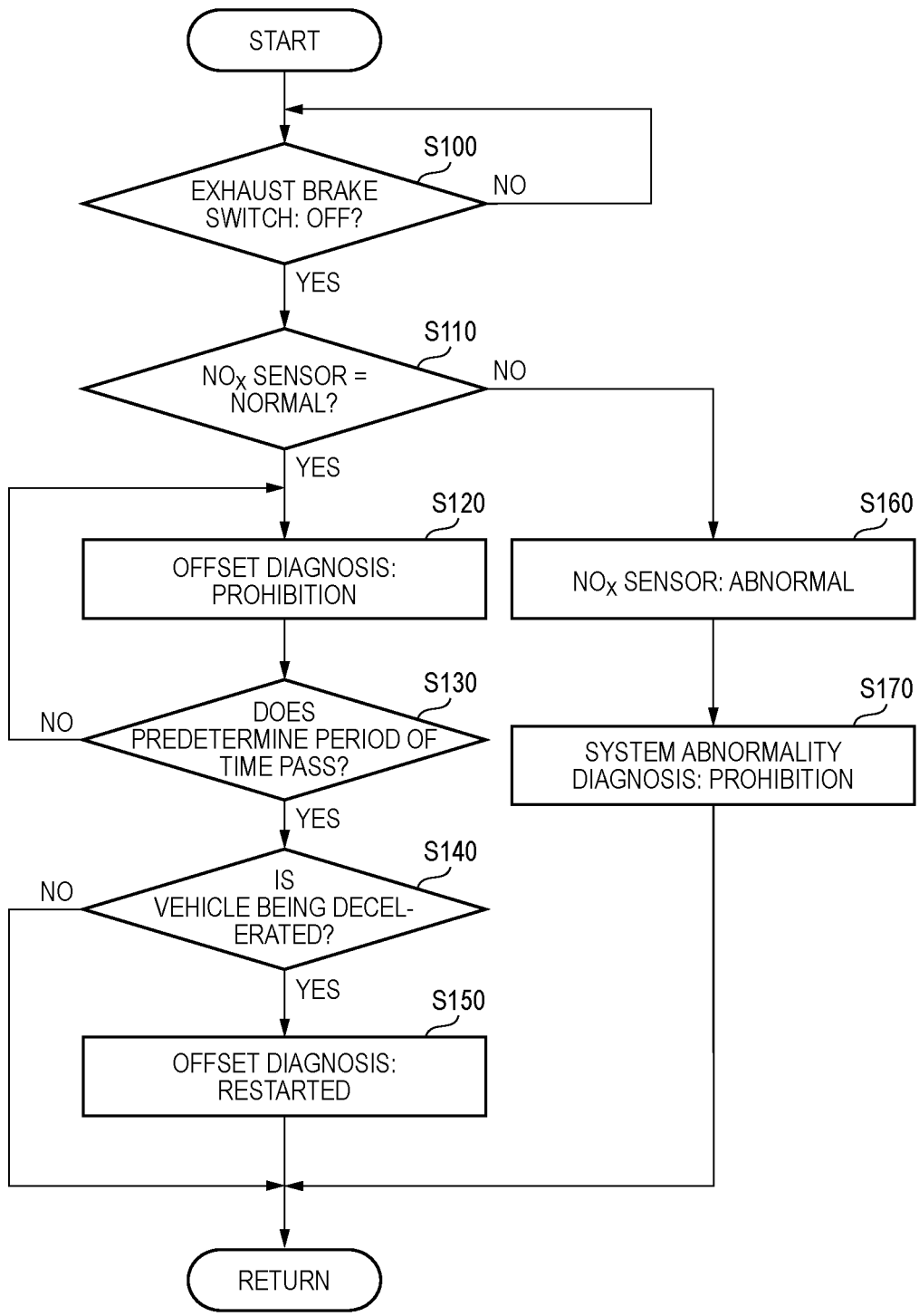
FIG. 4 is a flow chart explaining a diagnosis prohibition process of the present embodiment.

Next, the details of the diagnosis prohibition process of the present embodiment will be described with reference to a flow chart of FIG. 4. The diagnosis prohibition process is started when the offset diagnosis of the NOx sensor 100 is executed due to deceleration of the vehicle (stop of fuel injection of the engine 10) and also the exhaust brake device is switched on.

In step S100, it is determined whether or not the exhaust brake device is switched off. If the exhaust brake device is switched off (Yes), the process proceeds to step S110.

In step S110, sensor diagnosis of diagnosing whether or not an abnormality has occurred in the NOx sensor 100 is executed. When the peak value $S_{PEAK}$ of the sensor value $S_{NOx}$ exceeds the threshold, the process proceeds to step S160 and it is determined that an abnormality has occurred in the NOx sensor 100. The process further proceeds to step S170 and the system abnormality diagnosis using the NOx sensor 100 is prohibited. Then, the present control is returned.

In step S10, in a case where the peak value $S_{PEAK}$ of the sensor value $S_{NOx}$ is equal to or lower than the threshold, namely, in a case where the NOx sensor 100 is normal, the process proceeds to step S120 and the offset diagnosis of the NOx sensor 100 is prohibited.

In step S130, it is determined whether or not a predetermined period of time has passed after the offset diagnosis is prohibited. That is, the offset diagnosis is kept prohibited until the predetermined period of time has passed.

In step S140, it is determined whether or not the vehicle is still being decelerated (fuel injection is stopped). If the vehicle is being decelerated, the process proceeds to step S150 and the offset diagnosis of the NOx sensor 100 is restarted. On the other hand, if fuel injection of the engine 100 has been started due to acceleration of the vehicle or the like, the offset diagnosis is not restarted and the present control is returned.

As described in detail above, according to the diagnostic device of the present embodiment, by prohibiting the execution of the offset diagnosis of the NOx sensor 100 during a predetermined period of time at the time of switching of the exhaust brake from on to off at which the NOx sensor 100 outputs an abnormal value, it becomes possible to reliably prevent an erroneous diagnosis in which the abnormal sensor value is recognized as an offset amount from the zero point.

Meanwhile, the present invention is not limited to the above-described embodiments and modifications thereof can be appropriately made without departing from the spirit and scope of the present invention.

For example, the period of time, during which the offset diagnosis is prohibited, is not limited to switching of the exhaust brake device from on to off, but may include any other situations in which a flow rate of the exhaust gas rapidly increases during deceleration of the vehicle. Also, the engine 10 is not limited to the diesel engine, but the present invention may be widely applied to any other internal combustion engines, such as a gasoline engine.

This application is based on Japanese Patent Application No. 2015-038864 filed on Feb. 27, 2015, the entire contents of which are incorporated herein by reference.

INDUSTRIAL APPLICABILITY

According to the diagnostic device and the diagnostic system of the present invention, it is possible to effectively prevent an erroneous diagnosis in the offset diagnosis caused when a flow rate of the exhaust gas rapidly increases.

REFERENCE SIGNS LIST

10 Engine
11 Exhaust passage
12 Exhaust brake valve
13 Oxidation catalyst
14 Particulate filter
15 Urea adding valve
16 SCR catalyst
17 Accelerator opening sensor
18 Urea water tank
19 Urea water pump
20 Exhaust brake switch
40 Control unit
100 NOx sensor

The invention claimed is:

1. A diagnostic device for a sensor provided in an exhaust passage of an internal combustion engine of a vehicle and detecting nitrogen compounds in exhaust gas, the diagnostic device comprising:
   an offset diagnosis unit which diagnoses, during deceleration of the vehicle in which the internal combustion engine stops fuel injection, an offset amount of a sensor value of the sensor from a zero point based on the sensor value of the sensor; and
   a diagnosis prohibition unit which prohibits the diagnosing of the offset amount when a flow rate of the exhaust gas of the internal combustion engine rapidly increases while the offset amount is diagnosed by the offset diagnosis unit.

2. The diagnostic device according to claim 1, wherein the diagnosis prohibition unit prohibits the diagnosing of the offset amount when an exhaust brake device is switched from an operation state to a non-operation state.

3. The diagnostic device according to claim 2, wherein the diagnosis prohibition unit prohibits the diagnosing of the offset amount until a predetermined period of time has passed after switching to the non-operation state when the exhaust brake device is switched from the operation state to the non-operation state.

4. A diagnostic system comprising:
   a sensor provided in an exhaust passage of an internal combustion engine of a vehicle and detecting nitrogen compounds in exhaust gas; and
   a control unit,
   wherein the control unit is operated to execute:
   an offset diagnosis process of diagnosing, during deceleration of the vehicle in which the internal combustion engine stops fuel injection, an offset amount of a sensor value of the sensor from a zero point based on the sensor value of the sensor; and
   a diagnosis prohibition process of prohibiting the diagnosing of the offset amount when a flow rate of the exhaust gas of the internal combustion engine rapidly increases while the offset amount is diagnosed by the offset diagnosis process.

5. The diagnostic system according to claim 4, wherein, in the diagnosis prohibition process, the control unit prohibits the diagnosing of the offset amount when an exhaust brake device is switched from an operation state to a non-operation state.

6. The diagnostic system according to claim 5, wherein, in the diagnosis prohibition process, the control unit prohibits the diagnosing of the offset amount until a predetermined period of time has passed after switching to the non-operation state when the exhaust brake device is switched from the operation state to the non-operation state.

* * * * *